US012605357B2

(12) United States Patent
Silva

(10) Patent No.: US 12,605,357 B2
(45) Date of Patent: Apr. 21, 2026

(54) BIOACTIVE SUPPLEMENT

(71) Applicant: Wellington Silva, Ipatinga (BR)

(72) Inventor: Wellington Silva, Ipatinga (BR)

( * ) Notice: Subject to any disclaimer, the term of this patent is extended or adjusted under 35 U.S.C. 154(b) by 688 days.

(21) Appl. No.: 17/912,687

(22) PCT Filed: Feb. 4, 2021

(86) PCT No.: PCT/BR2021/050052
§ 371 (c)(1),
(2) Date: Sep. 19, 2022

(87) PCT Pub. No.: WO2021/184095
PCT Pub. Date: Sep. 23, 2021

(65) Prior Publication Data
US 2023/0172900 A1 Jun. 8, 2023

(30) Foreign Application Priority Data
Mar. 20, 2020 (BR) .......................... 1020200056271

(51) Int. Cl.
| | |
|---|---|
| *A61K 31/353* | (2006.01) |
| *A61K 31/05* | (2006.01) |
| *A61K 31/07* | (2006.01) |
| *A61K 31/122* | (2006.01) |
| *A61K 31/352* | (2006.01) |
| *A61K 31/381* | (2006.01) |
| *A61K 36/889* | (2006.01) |
| *A61K 38/06* | (2006.01) |

(52) U.S. Cl.
CPC ............ *A61K 31/353* (2013.01); *A61K 31/05* (2013.01); *A61K 31/07* (2013.01); *A61K 31/122* (2013.01); *A61K 31/352* (2013.01); *A61K 31/381* (2013.01); *A61K 36/889* (2013.01); *A61K 38/063* (2013.01)

(58) Field of Classification Search
CPC ...... A61K 31/353; A61K 31/05; A61K 31/07; A61K 31/122; A61K 31/381; A61K 36/889; A61K 38/063
See application file for complete search history.

(56) References Cited

U.S. PATENT DOCUMENTS

2010/0021533 A1 1/2010 Mazed

FOREIGN PATENT DOCUMENTS

| | | |
|---|---|---|
| WO | 2007011595 A2 | 1/2007 |
| WO | 2008154294 A1 | 12/2008 |
| WO | 2009105626 A1 | 8/2009 |

OTHER PUBLICATIONS

Pure Encapsulations. Manufacturer of hypoallergenic nutritional supplements. 2017. Available on: < https://www.pureencapsulations.com/media/PLs/2017 _PL_ Catalog_Price_web.pdf >.
Gupta C, Prakash D. Nutraceuticals for geriatrics. J Tradit Complement Med. 2014;5(1):5-14. Published Dec. 17, 2014. doi: 10.1016/j.jtcme.2014.10.004.
International Search Report, Instituto Nacional Da Propriedade Industrial, Apr. 19, 2021.

*Primary Examiner* — Marcos L Sznaidman
(74) *Attorney, Agent, or Firm* — Bay State IP, LLC

(57) ABSTRACT

The present disclosure relates essentially to a supplement, the function of which is to enhance immunity, prevent various diseases and assist in therapeutic treatments of various diseases, said supplement includes: 100 mg of lipoic acid, 1 mg of astaxanthin, 10 mg of glutathione, 5 mg of resveratrol, 5 mg of lycopene, 50 mg of epigallocatechin, 300 mg of curcumin, 400 mg of quercetin, 10 mg of coenzyme Q1 and 100 mg of dry açaí extract; formulated with the intention of combining substances that serve functions of assisting in the treatment of various diseases, such as: lipoic acid, which helps in the prevention of liver damage from intoxication, and can be used as a coadjuvant for the treatment of liver cirrhosis due to alcoholism and a coadjuvant for the treatment of diabetes and cataracts.

1 Claim, No Drawings

BIOACTIVE SUPPLEMENT

CROSS REFERENCE TO RELATED APPLICATION

This application is for entry into the U.S. National Phase from which priority is claimed under all applicable sections of Title 35 of the United States Code including, but not limited to, Sections 120, 363, and 365 (c) to International Application No. PCT/BR2021/050052 filed on Feb. 4, 2021, and which in turn claims priority under 35 USC 119 to Brazilian application Ser. No. 10/202,00056271 filed on Mar. 20, 2020.

INTRODUCTION

The present patent application for the Privilege of Invention refers to a supplement whose function is to increase immunity, prevent various diseases and assist in the therapeutic treatment of various diseases.

Said product, whose protection will be claimed in this report, was developed with the aim of filling deficiencies, alleviating difficulties and solving problems hitherto encountered by users of the sector, more precisely, sectors of Biochemistry and Pharmaceuticals.

FEATURES

The chemical composition in question, presented in this report, is composed of: 100 mg of Lipoic Acid, 1 mg of Astaxanthin, 10 mg of Glutathione, 5 mg of Resveratrol, 5 mg of Lycopene, 50 mg of Epigallocatechin, 300 mg of Curcumin, 400 mg of Quercetin, 10 mg of Coenzyme Q1 and 100 mg of dry acai extract.

FUNCTIONALITY

Initially, the aforementioned chemical composition, described in this report, will be used in the Biochemistry and Pharmacy sectors.

Formulated with the intention of bringing together substances that perform functions to help in the treatment of various diseases such as: Lipoic acid, which helps in the prevention of liver damage in intoxications; supporting in the treatment of liver cirrhosis in alcoholics, supporting in the treatment of diabetes and cataract.

Astaxanthin which helps prevent heart attacks, strengthens the immune system, helps lower blood glucose, helps prevent Alzheimer's and Parkinson's disease, improve recovery after stroke, normalize blood pressure, improve endurance to colds, it protects the brain, central nervous system, and eyes, increases physical resistance, reducing muscle damage; regulates inflammatory cytokines (Increased levels of these may predict the onset of rheumatoid arthritis).

Glutathione, in cancer prevention and aging prevention; Resveratrol, Platelet Aggregation Inhibitor; Fight against cholesterol (LDL); Improved flexibility of blood vessels; Cardioprotective.

Lycopene, helps in the effective action in the detoxification of people who smoke, drink and with a high fat diet; improves epithelial regeneration, prevents cellular aging; prevents the appearance of cancer; preventive against prostatic dysplasia; systemic protector against UV radiation.

Curcumin, helps in inflammatory bowel diseases; chronic pain; osteopathy; autoimmune diseases and Alzheimer's disease.

Quercetin, with anti-inflammatory function; antioxidant; acts on the immune system; has antiviral activity; reduces the effect of cataract formation in diabetics; hepatoprotective and gastroprotective and treatments for circulatory and capillary problems.

Coenzyme Q 10, an immune system stimulant, also used in mild and moderate congestive heart failure and degenerative diseases.

Epigallocatechin, acts as an anti-inflammatory, cardioprotective and chemoprotective agent.

The acai berry extract is indicated as an antioxidant, anti-inflammatory and reducer of bad cholesterol levels (LDL). In addition, the phytochemicals present in the composition of Açaí regulate enzymatic activities of metabolism, making the item act as a natural tonic for energy replacement. Phytochemicals also repair oxidative damage caused to DNA, prevent oxidative stress, decreasing the chances of developing diseases such as Parkinson's and Alzheimer's and keeping the immune system healthier.

The objective of this patent application is the development of a new substance capable of obtaining the concentration of bioactive compounds. In research carried out in medical/scientific production databases, there is no result on what is being proposed.

The manufacturing will be done by combining nine Components: 100 mg of Lipoic Acid, 1 mg of Astaxanthin, 10 mg of Glutathione, 5 mg of Resveratrol, 5 mg of Lycopene, 50 mg of Epigallocatechin, 300 mg of Curcumin, 400 mg of Quercetin, 10 mg of Coenzyme Q1 and 100 mg of dry acai extract.

INNOVATION

In general terms, the aforementioned chemical composition represents a solution capable of obtaining the concentration of bioactive compounds.

The supplement will act in different ways, as mentioned above in the functions of each component: helping to increase immunity and helping to protect from various diseases. Therefore, there is no mechanism per se for this formulation, the activity is based on the joint action of its components.

One of the advantages is the action in the prevention of several diseases in several organs such as: heart, blood vessels, prostate, brain, liver, eyes. It can also be mentioned as an advantage that the intake of this supplement mimics the intake of various foods and in significant amounts, which would save money and effort for the user, not to mention the health gain as mentioned.

It is also important to emphasize the following advantages: Helps in the prevention and treatment of degenerative diseases, such as Alzheimer's, helps in the prevention and treatment of cardiovascular diseases, such as heart attack, helps in the prevention and treatment of diabetes, atherosclerosis and skin aging and helps in the prevention and treatment of cancer.

DESCRIPTION OF THE STATE OF THE TECHNIQUE

During the development of the aforementioned chemical composition, numerous researches were carried out to identify the existence of possible prior art or similar compositions. Such surveys, however, did not point to the existence of any other composition with the same preponderant technical or functional characteristics.

In view of this need and commercial opportunity, the aforementioned composition was created, more precisely a combination of nine components: 100 mg of Lipoic Acid, 1 mg of Astaxanthin, 10 mg of Glutathione, 5 mg of Resveratrol, 5 mg of Lycopene, 50 mg of Epigallocatechin, 300 mg of Curcumin, 400 mg of Quercetin, 10 mg of Coenzyme Q1 and 100 mg of dry acai extract.

Therefore, in accordance with article 8 of the Industrial Property Law No. 9.279/96 and for all the aspects presented in this report, the object of this patent application is worthy of protection as a Privilege of Invention, which is now claimed.

What is claimed is:

1. A bioactive supplement comprising:

100 mg of Lipoic Acid;

1 mg of Astaxanthin;

10 mg of Glutathione;

5 mg of Resveratrol;

5 mg of Lycopene;

50 mg of Epigallocatechin;

300 mg of Curcumin;

400 mg of Quercetin;

10 mg of Coenzyme Q10; and 100 mg of dry acai extract.

\* \* \* \* \*